United States Patent [19]

Honda

[11] Patent Number: 5,285,823
[45] Date of Patent: Feb. 15, 1994

[54] APPARATUS AND METHOD FOR EVACUATING BLOOD ASPIRATION TUBES

[75] Inventor: Kiyoteru Honda, Sasebo, Japan

[73] Assignee: Daiichi Industries Corporation, Nagasaki, Japan

[21] Appl. No.: 763,102

[22] Filed: Sep. 20, 1991

[30] Foreign Application Priority Data

Oct. 2, 1990 [JP] Japan ................................ 2-65593
Jun. 24, 1991 [JP] Japan ................................ 3-180322

[51] Int. Cl.$^5$ .......................... G01N 3/02; B65B 35/56
[52] U.S. Cl. ........................................ 141/7; 141/65; 141/130; 141/329; 141/237; 422/100; 73/863.85; 73/864.25
[58] Field of Search ............... 141/1, 5, 7, 65, 130, 141/236–238, 329; 53/403, 405, 408, 432, 510; 73/864.24, 864.25, 864.52, 864.86, 863.85; 422/100

[56] References Cited

U.S. PATENT DOCUMENTS

| | | | |
|---|---|---|---|
| 2,562,815 | 7/1951 | Oscroft | 141/236 |
| 4,063,460 | 12/1977 | Svensson | 141/65 |
| 4,106,911 | 8/1978 | Marcelli | 141/237 |
| 4,140,018 | 2/1979 | Maldarelli et al. | 73/864.25 |
| 4,757,437 | 7/1988 | Nishimura | 73/864.25 |
| 4,854,355 | 8/1989 | Chazot et al. | 141/130 |
| 4,865,090 | 9/1989 | Burolla et al. | 141/329 |
| 4,951,512 | 8/1990 | Mazza et al. | 141/130 |
| 5,055,263 | 10/1991 | Meltzer | 73/864.24 |
| 5,067,532 | 11/1991 | Lang et al. | 141/130 |
| 5,084,242 | 1/1992 | Sakuma et al. | 73/864.25 |

*Primary Examiner*—Ernest G. Cusick
*Attorney, Agent, or Firm*—Ostrager, Chong & Flaherty

[57] ABSTRACT

An apparatus for automatically evacuating blood aspiration tubes has an arraying table supporting a number of stoppered blood aspiration tubes which are to be evacuated, an air suction needle for evacuating air from inside the stoppered blood aspiration tubes, and an arm supporting the air suction needle on a needle rest and moving it horizontally and vertically over the arraying table. A drive control moves the air suction needle downward into the stopper of each of the blood aspiration tubes in turn, causes the needle to evacuate air from the tube, then withdraws the needle upward from the stopper. A presser is mounted to a lower part of the needle rest and presses the stopper during the upward movement of the needle in order to maintain the airtight stoppering of the tube.

7 Claims, 6 Drawing Sheets

APPARATUS AND METHOD FOR EVACUATING BLOOD ASPIRATION TUBES

BACKGROUND OF THE INVENTION

1. Field of the Invention

This invention relates to production of a blood drawing or aspiration tube which is used in a vacuum state by medical organizations for obtaining a blood sample for blood analyses. More particularly, it relates to an apparatus for automatically evacuating a blood aspiration tube, whereby air may be automatically expelled from the interior of the stoppered blood aspiration tubes to produce a blood aspiration tube maintain in vacuum.

2. Description of Relates Art

In medical organizations, blood samples are produced for detection of possible diseases. Conventionally, blood samples were obtained using a syringe. More recently, blood aspiration tubes are used in an increasing number for blood sampling.

The blood aspiration tube is a transparent test tube which is stoppered by a rubber stopper and has a vacuum maintained inside. For blood sampling with the aid of the blood aspiration tube, a syringe having needles at both ends is used. One needle is introduced into the patient's skin and the other needle is inserted in the rubber stopper of the blood aspiration tube. Since the interior of the blood aspiration tube is maintained in vacuum, the blood is automatically sucked into the blood aspiration tube for blood sampling.

Since blood sampling may be achieved easily by using the blood aspiration tube, it is used in an increasing number by, e.g., medical organizations.

For producing the above-mentioned blood aspiration tube, it is necessary to evacuate the inside of the blood aspirator tube before it fitted with the rubber stopper. This is accomplished by inserting the rubber stopper when the blood aspiration tube is within a vacuum chamber. However, the operation in the vacuum chamber necessitate the use of various devices such as a manipulator and equipment including the vacuum chamber itself which raises production costs.

OBJECT AND SUMMARY OF THE INVENTION

In view of the foregoing, it is an object of the present invention to provide an apparatus for automatically evacuating a blood aspiration tube whereby air may be automatically sucked from the inside of the stoppered blood aspiration tube to enable production of the blood aspiration tube, the inside of which is maintained in a vacuum state, by a relatively simplified production system.

In accordance with the present invention, there is provided an apparatus for automatically evacuating a blood aspiration tube comprising an arraying table on which a number of stoppered blood aspiration tubes to be evacuated are arrayed at a predetermined pitch, an air suction needle for sucking air from the inside of the stoppered blood aspiration tubes for evacuation, driving means for moving said air suction needle horizontally and vertically relative to said arraying table, a presser for Pressing a stopper of said blood aspiration tube during vertical upward movement of said air suction needle, an air suction unit for sucking air through said air suction needle, and a controlling device for controlling the operations of said air suction needle, presser and air suction unit for automatically sucking air from the inside of said blood aspiration tube maintained in a tightly sealed state.

In operation, a number of stoppered and tightly sealed blood aspiration tubes, the inside of which is maintained in vacuum, are arrayed on an arraying table, and predetermined input conditions are inputted into the controlling device. The controlling apparatus is then set into operation. The air suction needle, adapted to be movable horizontally and vertically, is moved horizontally on top of the stoppered blood aspiration tubes, arrayed at a predetermined pitch, until positioned directly above a selected one of the stoppered blood-drawing tubes.

The air suction needle then descends so that its distal end pierces through the stopper of the blood aspiration tube to enter the inside of the tightly sealed tube to suck air from the aspiration tube by actuation of the air suction unit to establish a vacuum within the aspiration tube.

When a vacuum is established within the blood aspiration tube, the air suction needle is raised. A presser adapted for pressing the stopper of the blood aspiration tube during upward travel of the air suction needle, is lowered at this time to press the stopper of the blood aspiration tube so that the stopper will not be lifted with the vacuum suction needle, thus the vacuum suction needle may be extricated smoothly from the stopper of the blood aspiration tube as the needle is uplifted.

The needle is then moved horizontally to a position directly above the neighboring stoppered blood aspiration tube to suck the air from its inside in a similar manner. By repetition of the above described sequence of operations, evacuation of the inside of the stoppered blood aspiration tubes may be achieved automatically.

In this manner, it is possible with the apparatus of the present invention to automatically evacuate the inside of the stoppered blood aspirator tube, so that the blood aspiration tube having its interior maintained in vacuum may be produced automatically. Since manual labor may be dispensed with, the operator may perform other jobs during production of the blood aspiration tubes for improving operational efficiency.

Since air may be sucked automatically from the inside of the stoppered blood aspiration tube, the evacuated blood aspiration tube may be produced by a relatively simple production system with outstanding practical advantages.

THE BEST MODE OF THE INVENTION

First Embodiment

Figure 1:
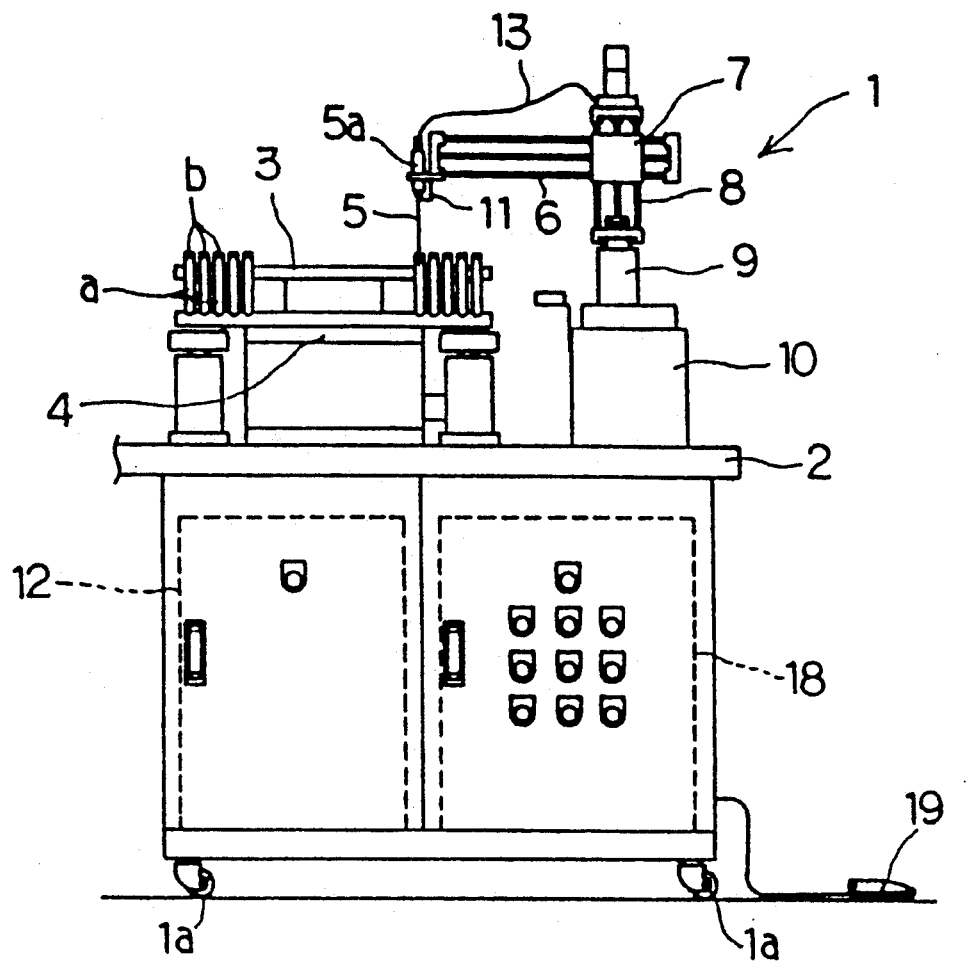
FIG. 1 is a side view showing an apparatus for automatically evacuating a blood aspiration tube according to a first embodiment of the Present invention.
Figure 2:
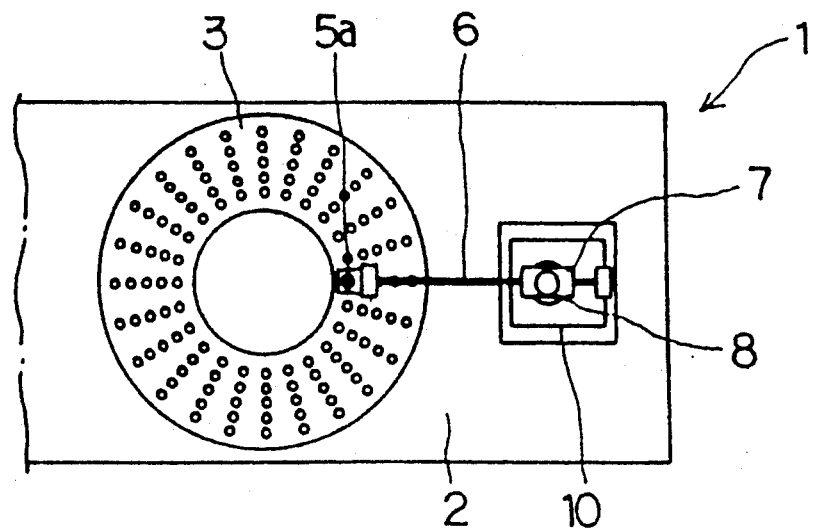
FIG. 2 is a plan view of the first embodiment.
Figure 3:
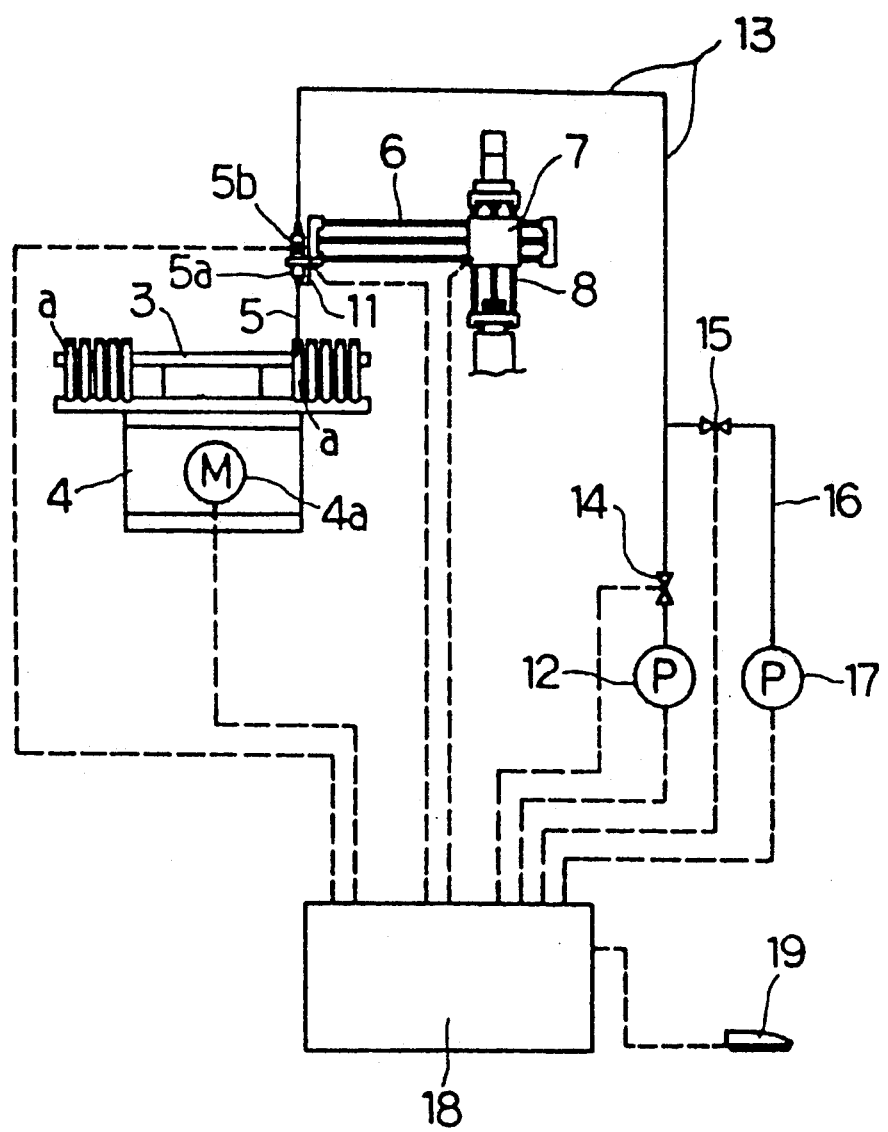
FIG. 3 is a schematic view showing a controlling system for the apparatus shown in FIGS. 1 and 2.
Figure 4:
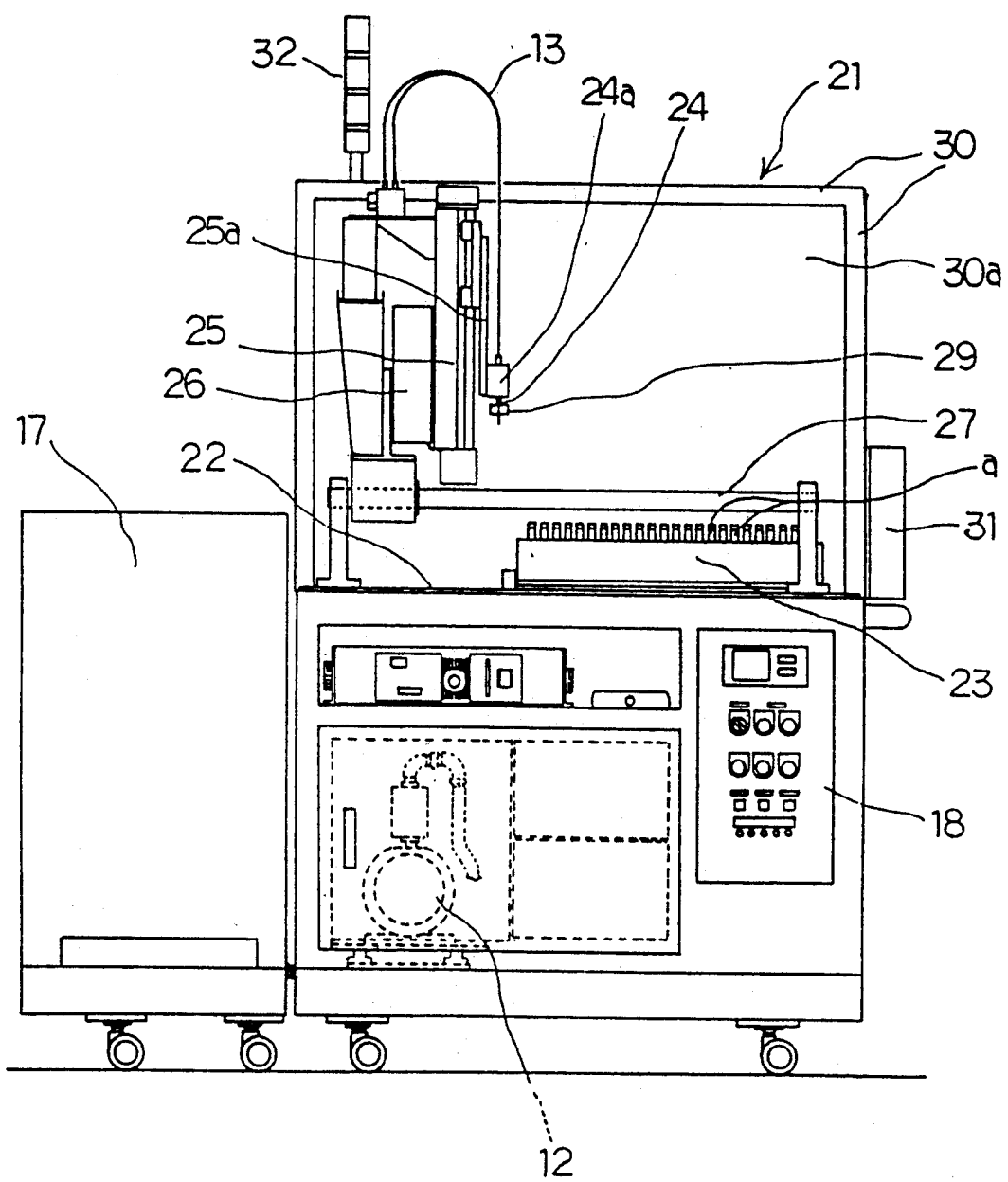
FIG. 4 is a side view showing an apparatus for automatically evacuating a blood aspiration tube according to a second embodiment of the present invention.
Figure 5:
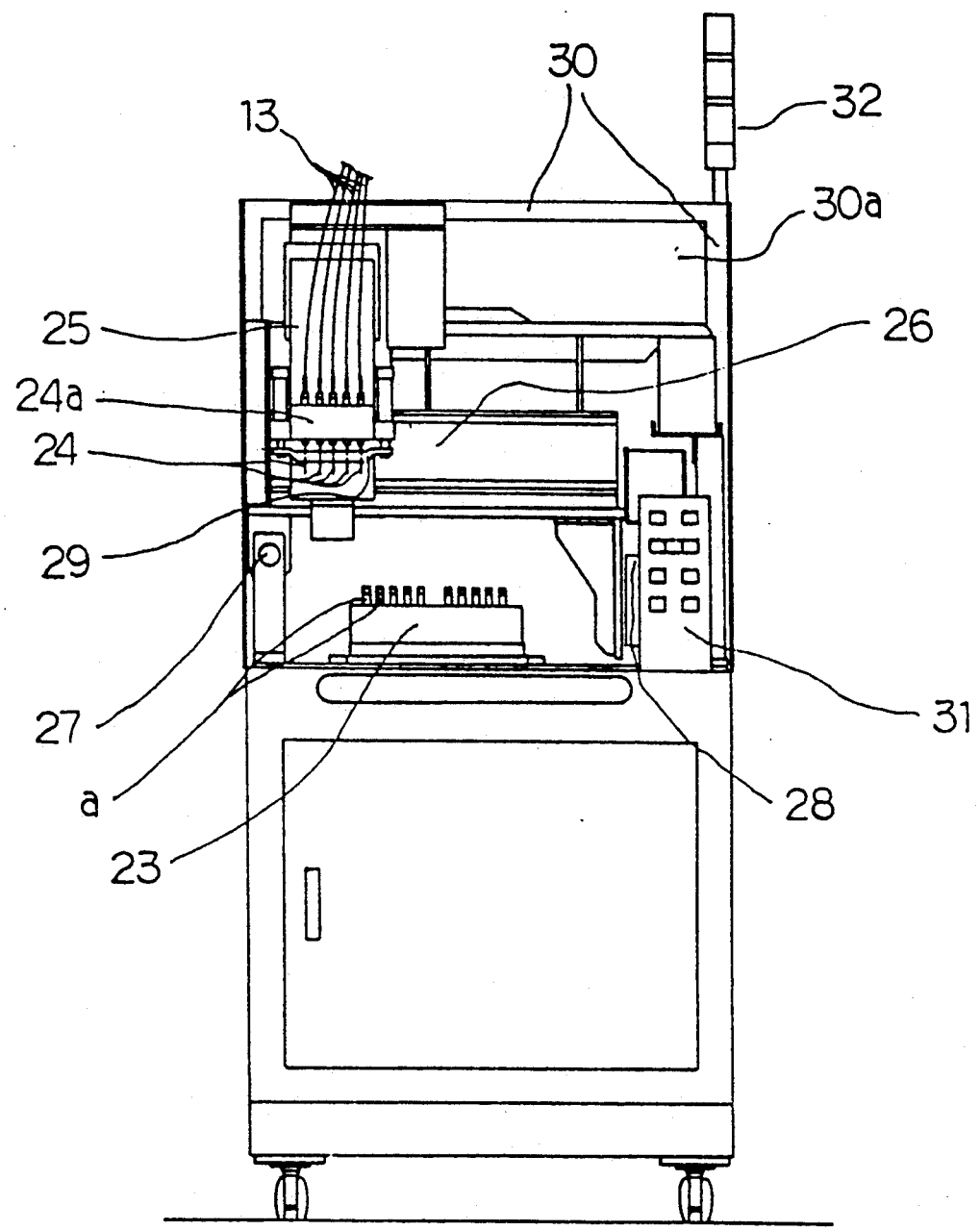
FIG. 5 is a front view of the second embodiment.

Certain preferred embodiments of the present invention will be explained in more detail with reference to the drawings, wherein:

Referring to FIGS. 1 through 3, the evacuating apparatus 1 is adapted for automatically sucking air from the inside of blood aspiration tubes a, each fitted with a rubber stopper b, for producing evacuated blood aspiration tubes a.

At the middle of a table-shaped base plate 2 of the automatic evacuating apparatus for blood aspiration tubes, there is mounted a disk-shaped arraying table 3, on which a number of the blood aspiration tubes a to be evacuated are arrayed. A large number of blood aspirator tubes a are arrayed at a predetermined interval both circumferentially and radially towards the periphery of the disk-shaped arraying table 3. The upper open ends of the blood aspiration tubes a arrayed on the table 3 are stoppered by rubber stoppers b for hermetically sealing the inside of the tubes a.

The arraying table 3 is mounted on a rotary base 4 installed on the base plate 2. A driving electric motor 4 is enclosed within the interior of the rotary base 4. BY the rotational power of the driving motor, the rotary base 4a is driven rotationally for rotating the arraying table 3 mounted thereon. Although the arraying table 3 is shown in FIG. 2 as being disk-shaped, it may also be rectangular in contour.

An air suction needle 5 is provided on top of the arraying table 3 on which the blood aspiration tubes a are arrayed. The air suction needle 5 is a device for drawing air from the inside of the blood aspiration tube a stoppered by the rubber stopper b. The air suction needle 5 is similar in construction to a syringe needle and has an internal air passage along the needle axis communicating with an air suction unit 12 via air suction passage 13, which will described hereinafter.

The air suction needle 5 is mounted with the distal end thereof directed downwards and with the upper end thereof mounted in a needle nest 5a. The needle rest 5a, which supports the air suction needle 5, is supported for vertical movement within a distal end part of a horizontal arm 6. A pressure sensor 5b is attached to the needle rest 5a. When the air suction needle 5 pierces through the rubber stopper b of the blood aspiration tube a, pressure sensor 5b senses the pressure acting on the air suction needle 5.

The pressure sensor 5b is connected to a controlling unit 18, which will be described later, so that data sensed by the pressure sensor 5b is transmitted to the controlling unit 18, which then detects automatically if the air suction needle 5 has correctly pierced through the rubber stopper b of the blood aspirator tube a. The horizontal arm 6, to which the air suction needle 5 is attached by way of the needle rest 5a, is mounted on a vertically movable base block 7 for horizontal movement. The base block 7, which supports the horizontal arm 6, is mounted on a vertically movable arm 8 for vertical movement. The arm 8 has its lower end supported by a supporting block 9. The supporting block 9 has its lower end mounted on a frame 10 in turn mounted on the base plate 2.

Since the air suction needle 5 is mounted for vertical movement on the horizontal arm 6 via needle rest 5a and the horizontal arm 6 mounting the air suction needle 5 is mounted for horizontal movement on the base block 7, which is mounted so as to movable vertically along the vertical arm 8, the air suction needle 5 is movable both horizontally and vertically. A presser 11 is attached to a lower part at the distal end of the horizontal arm 6 to which the air suction needle 5 is mounted by means of needle rest 5a. The presser 11 acts on the rubber stopper b of the blood aspiration tube a during upward movement of the air suction needle 5 to Prevent the rubber stopper b and the blood aspiration tube a, into which the air suction needle 5 has been introduced, from being moved upwards simultaneously with the air suction needle 5.

The presser 11 extends downwards and has its lower part bent horizontally and bifurcated so that the air suction needle 5 is introduced downwards in a gap defined between bifurcated ends.

The air suction unit 12 is designed to suck air from the inside of the blood aspiration tubes a by way of the air suction needle 5, and is provided below the base plate 2 of the automatic evacuator 1. The air suction unit 12 is constituted by a vacuum pump etc. and connected to one end of an air suction conduit 13, to the other end of which is connected the air suction needle 5, so that the air suction unit 12 and the needle 5 communicate with each other by the air suction conduit 13. A vinyl hose, for example, is used as the conduit 13.

A changeover valve 14 (see FIG. 3) for turning the communication between the air suction needle 5 and the air suction unit 12 on and off is provided at a connecting portion between the air suction unit 12 and the air suction conduit 13.

A second changeover valve 15 for turning the outflow of compressed air on and off is provided halfway between air suction conduit 13 upstream of the suction control changeover valve 14. One end of a compressed air blowout conduit 16 is connected to changeover value 15; the other end of conduit 16 is connected to a compressed air blowout unit 17, which may be constituted by e.g. a compression pump, not shown.

The controlling unit 18 controls various operations, such as horizontal and vertical movement of the air suction needle 5, rotation of the arraying table 3, operation of the presser and actuation of the air suction unit 12. BY controlling these operations, the controlling unit 18 plays the role of automatically sucking air from the inside of the blood aspiration tube a tightly sealed by the rubber stopper b.

The controlling unit 18 is provided adjacent to the air suction unit 12 below the base plate 2 of the automatic evacuator 1.

The air suction needle 5 is controlled in its horizontal movement and vertical movement by controlling the needle rest 5a, horizontal arm 6 and vertical arm 8, while the arraying table 3 is controlled in its rotational movement by controlling the driving motor 4a for rotary base 4.

The controlling unit 18 also controls the operation of the suction control changeover valve 4, compressed air blowout control changeover valve 15 and the compressed air blowout unit 17 etc.

A line from the presser 5b is connected to the controlling unit 18, which performs the above described controlling operation, so that data from pressure sensor 5b may received thereby.

A foot switch 19 is adapted to start or stop the automatic evacuator 1 by being pressed by the user's foot.

The lower end of the automatic evacuator 1 is fitted with casters 1a to facilitate movement of the evacuator.

The operation of the above-described first embodiment will be hereinafter explained.

The rubber stopper b is fitted on the opened upper end of the blood aspiration tube a for tightly sealing the blood aspiration tube a. A number of such blood aspiration tubes a, fitted with rubber stoppers b, are prepared. These blood aspiration tubes a are arrayed on the arraying table 3. On the other hand, a power source switch of the automatic evacuator 1 is turned on, and an auto-/manual changeover switch is switched to an auto state. This initiates the operation of the air suction unit 12 and the controlling unit 18, while actuating the horizontal arm 6, vertical movable base block 7 and needle rest 5a and setting the air suction needle 5 at a start Position. At this time, prescribed input conditions, such as the number of the blood aspiration tubes a arrayed on the arraying table 3, are entered into the controlling unit 18.

It is also checked, by indicating lamps associated with various devices, if these devices are operating normally. The indicating lamps indicate the normal operating state by being lit continuously or intermittently.

The compressed air blowout unit 17 is then started to open the compressed air blowout control changeover valve 15 to permit compressed air to flow from the unit 17 via compressed air blowout conduit 16 and the air suction conduit 13 towards the air suction needle 5 so as to be discharged at the distal end of the air suction needle 5. In this manner, it is confirmed that air does flow through the air suction needle 5, with the indicating lamps being lit continuously or intermittently to indicate the normal operating state of the air suction needle 5.

The compressed air blowout control changeover valve 15 is then closed. After checking by indicating lamps that the various devices are in normal operating states, the foot switch 19 is pressed by the operator to start the operation of the automatic evacuator 1.

When the foot switch 19 is turned on, the control operation of the controlling unit 18 is initiated. The horizontal arm 6, on the distal end of which is attached the air suction needle 5 via needle rest 5a, is moved forwards relative to the base block 7, in response to control commands from the controlling unit 18. The forward travel of the arm 6 ceases when the air suction needle 5 at the distal end of the horizontal arm 6 reaches a position directly above the blood aspiration tube a arrayed on the table 3.

The needle rest 5a, to which the air suction needle 5 is attached, then descends in response to control commands from the controlling unit 18, so that the distal end of the needle 5 abuts and pierces through the rubber stopper b of the blood aspiration tube a, with the distal end of the needle 5 intruding into the inside of the tightly sealed blood aspiration tube a. When the distal end of the air suction needle 5 has pierced through the rubber stopper b so as to intrude into the interior of the blood aspiration tube a, this state is sensed by the pressure sensor 5b of the needle rest 5a and corresponding data are transmitted to the controlling unit 18.

Based on the data from pressure sensor 5b, the controlling unit 18 detects that the distal end of the air suction needle 5 has been properly inserted into the interior of the blood aspiration tube a, and transmits a command for opening the suction controlling changeover valve 14, which is thereby opened.

Upon opening of the suction controlling changeover valve 14, suction through the air suction needle 5, which has been introduced into the interior of the blood aspiration tube a, starts so that air within the interior of the blood aspirator aspirator tube a is sucked through the needle 5 to establish a vacuum inside the blood aspiration tube a. The air sucked by the air suction needle 5 is expelled to the outside via suction conduit 13. The indicating lamps are lit continuously or intermittently to indicate that a vacuum has been established in the interior of air suction needle 5.

The suction time period is 2 to 3 seconds in the preferred embodiments, but may be suitably changed and set depending on the ability of the air suction unit 12, the inner capacity of the blood aspiration tube a, etc.

After lapse of the suction time period, the controlling unit 18 issues a command for valve closure to the suction controlling changeover valve 14, which is thereby closed.

Upon termination of the evacuation of the blood aspiration tube a, the controlling unit 18 issues a command for upward vertical movement to the needle rest 5a. In response to this command, the needle rest 5a supporting the air suction needle 5 is raised. The presser 11, provided below the needle rest 5a, acts on the rubber stopper b of the blood aspiration tube a from above, to prevent the rubber stopper b, pierced by the air suction needle 5, and the blood aspiration tube a, from being uplifted simultaneously with the blood aspiration needle 5.

By the function of the presser 11, the distal end of the air suction needle 5 may clear the rubber stopper b. The needle hole produced upon extrication of the distal end of the air suction needle 5 is instantly sealed due to the inherent of elasticity the material of the rubber stopper b to prevent air from flowing into the interior of the blood aspiration tube a. Thus the blood aspiration tube a with an interior maintained at vacuum is produced.

When the needle rest 5a is raised to a predetermined height and the distal end of the air suction needle 5 completely clears the rubber stopper b, the controlling unit 18 issues a command for vertical movement to the base block 7 which then is moved vertically with the horizontal arm 6 supported thereby.

As the horizontal arm 6 is raised, the air suction needle 5 and the presser 11 are similarly raised to a predetermined height. The horizontal arm 6 is then moved horizontally until it is halted when the air suction needle 5 reaches a position directly above the neighboring blood aspiration tube a.

A similar sequence of operations is Performed under the commands from the controlling unit 18 so that, by repetition of the similar operations, evacuation of the blood aspiration tubes a tightly sealed by rubber stoppers b is achieved automatically.

Upon completion of the evacuation of the blood aspiration tubes a of the same row, the air suction needle 5 is reverted to its start position in response to a command from the controlling unit 18. In response to commands from the controlling unit 18, the driving motor 4a drives the rotary base 4. By the rotation of the rotary base 4, the arraying table 3 is similarly rotated for bringing unevacuated blood aspiration tubes a of the neighboring row below a range of movement of the air suction needle 5. A sequence of similar evacuating operations is then performed automatically.

The controlling unit 18 operates under the input conditions to count the number of blood aspiration tubes a arrayed on the table 3 to suck air from the inside of all of the blood aspiration tubes a on the table 3. The operation is terminated upon termination of the evacuating operations under the present input conditions.

Second Embodiment

As can be seen in FIGS. 4 through 7, the second embodiment differs appreciably from the first embodiment in that a plurality of air suction needles are provided so that a plurality of blood aspiration tubes a may be evacuated simultaneously, and in that, while the arraying table 3 of the first embodiment is rotatable, the arraying table of the second embodiment is fixed and the air suction needles are movable in the fore-and-aft and left-and-right directions on the fixed arraying table for evacuation.

Figure 6:
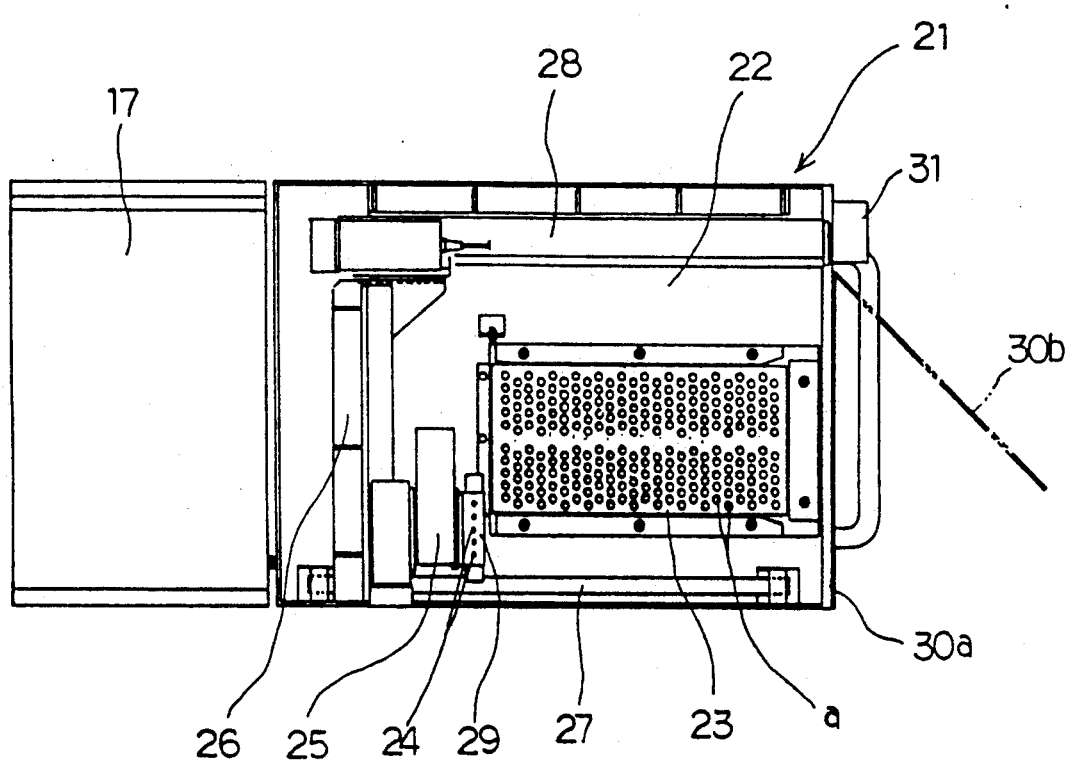
FIG. 6 is a plan view of the second embodiment.
Figure 7:
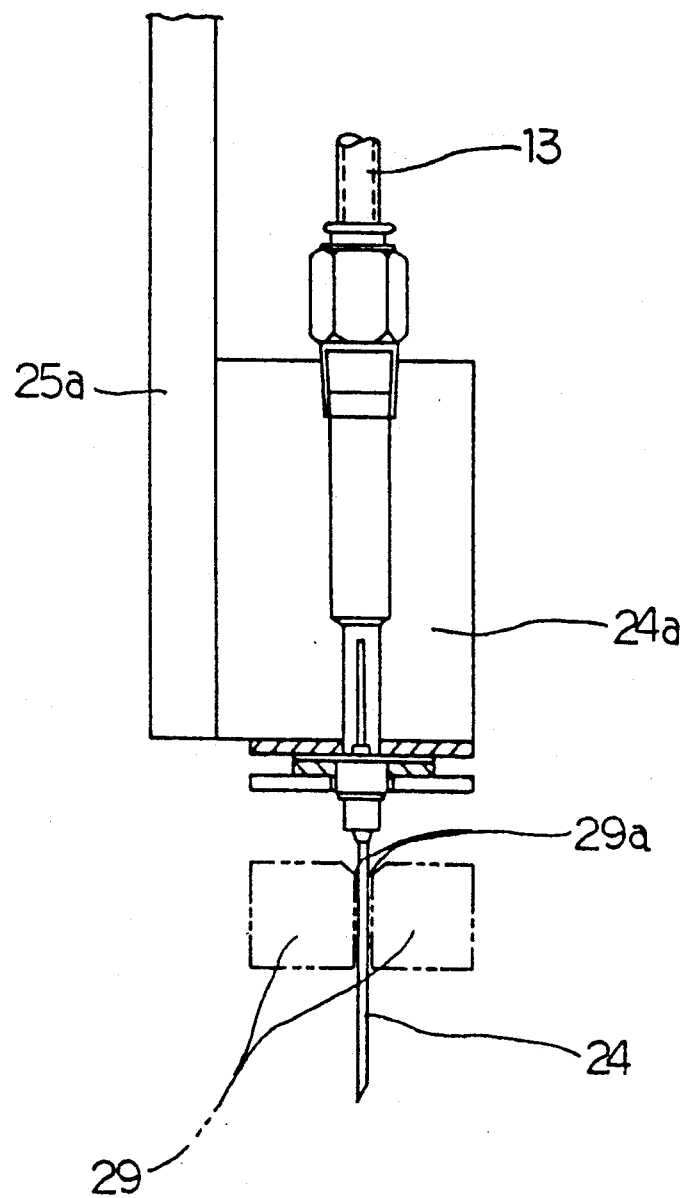
FIG. 7 is an enlarged side view showing a needle rest employed in the apparatus shown in FIGS. 4 to 6.

Referring to FIG. 6, it can be seen that in accordance with the second embodiment, an arraying table 23, on which blood-drawing tubes a to be evacuated are arrayed at a predetermined pitch, is provided at the middle of a table-shaped base plate 22. A large number of blood aspiration tubes a are arrayed at a predetermined pitch in a latticed or staggered relation in the for-and-aft and left-and-right directions on the arraying table 23, which, for example, is rectangular in contour.

A plurality of air suction needles 24 are arrayed in the left-and-right direction and mounted in their entirety on a needle rest 24a (see FIGS. 5 and 7) so that the air suction needles 24 may be moved in unison by the movement of the needle rest 24a in the vertical, fore-and-aft and left-and-right directions.

Since a plurality of blood aspiration tubes 24 may be evacuated simultaneously, the evacuating ability is improved significantly over the first embodiment.

The needle rest 24a, carrying a plurality of air suction needles 24, is mounted for vertical movement on an upstanding base block 25. This is, the needle rest 24a is mounted at the lower end of a vertically movable block 25a movable vertically along the upstanding base block 25. The base block 25, on which the suction needles 24 are attached by means of the needle rest 24a and the block 25a, is mounted on a horizontal base block 26 for movement horizontally in the left-and-right directions.

The horizontal base block 26, on which the upstanding base block 25 is mounted, has both of its ends supported by a horizontal supporting arm 27 and a horizontal driving arm 28, so that the horizontal base block may be moved horizontally in the fore-and-aft directions along the horizontal supporting arm 27 and the horizontal driving arm 28 by actuation of the horizontal driving arm 28. These arms 27, 28 are arranged horizontally along the fore-and-aft directions on the left-and-right sides on the base plate 22.

A presser 29 is attached to a lower part of the upstanding base block 25 to which the air suction needles 24 are attached by means of the needle rest 24a. The presser 29 is designed to act on the rubber stoppers b of the blood aspiration tubes a during upward movement of the air suction needles 24 to prevent the stoppers b and the blood aspiration tubes a, into which the air suction needles 24 have been introduced, from being raised simultaneously with the air suction needles 24.

The presser 29 has its left and right sides supported by the vertically movable block 25a, and is formed with a plurality of needle apertures 29a, through which the air suction needles 24 are passed for extending downwards.

A frame 30 is provided above the base plate 22 of the automatic evacuator 21, and a transparent Plastic plate 30a is provided on the frame 30 for protecting various devices provided on the base plate 22. The frame 30 is fitted with a transparent door 30b through which the blood aspiration tubes a on the base plate 22 may be introduced or taken out of the apparatus. A switchboard 31 is mounted laterally of the door 30b.

A signal pole 32 is mounted on the top of the frame 30 and provided with red, blue and yellow indicating lamps, for example, when viewed from above. The red, blue and yellow indicating lamps on the signal pole 32 are lit intermittently during the operation of evacuating the blood aspiration tubes a by the air suction needles 24, upon termination of the operation and during abnormal operation, respectively.

Since the construction of the second embodiment is otherwise the same as that of the first embodiment, the corresponding description is omitted for simplicity.

It is to be noted that the present invention is not limited to the above embodiments, but may comprise various modifications within the spirit and scope of the invention defined in the appended claims.

What is claimed is:

1. A method for automatically evacuating blood aspiration tubes comprising the steps of:

stoppering a number of blood aspiration tubes in an atmospheric pressure environment with rubber stoppers inserted in upper ends thereof for tightly sealing the inside of said blood aspiration tubes, placing a number of stoppered blood aspiration tubes in a predetermined array on an arraying table, mounting a plurality of air suction needles on a needle rest movable over said stoppered blood aspiration tubes, moving said needle rest carrying said plurality of air suction needles along a horizontal path and a vertical path over said stoppered blood aspiration tubes arrayed on said arraying table, and driving said air suction needles with a downward vertical movement into the stoppers of respective ones of said blood aspiration tubes and, after evacuation of said blood aspiration tubes, withdrawing said air suction needles with an upward vertical movement from said stoppers, sucking air simultaneously through said air suction needles so as to evacuate the inside of said blood aspiration tubes with a vacuum, extracting said blood aspiration needles while pressing the stoppers of said blood aspiration tubes, by mounting a presser to a lower part of said needle rest and pressing said stoppers during upward vertical movement of said air suction needles such that said stoppers are prevented from moving upwards as said air suction needles are withdrawn, and repeating the moving, sucking and extracting steps for a plurality of sets each consisting of a plurality of stoppered blood aspiration tubes.

2. An apparatus for automatically evacuating blood aspiration tubes comprising:

an arraying table on which a number of stoppered blood aspiration tubes to be evacuated are arrayed vertically with respective rubber stoppers inserted in their upper ends for stoppering and tightly sealing said blood aspiration tubes, a horizontal arm mounted over said blood aspiration tubes on said arraying table, an air suction needle for sucking air from the inside of one of said stoppered blood aspiration tubes for evacuation, said air suction needle being carried on a needle rest which is movably mounted on said horizontal arm, driving means for moving said needle rest carrying said air suction needle along a horizontal path and a vertical path over said stoppered blood aspiration tubes arrayed on said arraying table, and for driving said air suction needle with a downward vertical movement into a stopper of one of said blood aspiration tubes and, after evacuation of said one of said blood aspiration tubes, withdrawing said air suction needle with an upward vertical movement from said stopper, a presser for pressing said stopper of said one of said blood aspiration tubes during upward vertical movement of said air suction needle, said presser being mounted to a lower part of said needle rest and being arranged to press said stopper during upward vertical movement of said air suction needle such that said stopper is prevented from moving upwards as said air suction needle is withdrawn, an air suction unit for sucking air through said air suction needle so as to evacuate the inside of said one of said blood aspiration tubes with a vacuum, and a controlling device for controlling the operation of said air suction needle, said presser and said air suction unit for automatically sucking air from the inside of said one of said blood aspiration tubes maintained in a tightly sealed state.

3. The apparatus as claimed in claim 2, further comprising compressed air blowout means fluidically connected to said air suction needle for ascertaining that the air has passed through said air suction needle.

4. The apparatus of claim 2, wherein said presser extends downward from the lower part of said needle rest and has a lower part which is bent horizontally over the stopper of said one of said blood aspiration tubes and is bifurcated with a gap between opposing bifurcated ends thereof so that the air suction needle is driven downwards and withdrawn upwards through the gap between said bifurcated ends.

5. The apparatus of claim 2, further comprising a pressure sensor coupled to said air suction needle on said needle rest and to said controlling device, for detecting if the air suction needle has correctly pierced through the rubber stopper of said one of said blood aspiration tubes, and for thereupon transmitting data to said controlling unit for actuating said air suction unit.

6. An apparatus for automatically evacuating blood aspiration tubes comprising:

an arraying table on which a number of stoppered blood aspiration tubes to be evacuated are arrayed vertically with respective rubber stoppers inserted in their upper ends for stoppering and tightly sealing said blood aspiration tubes, a horizontal arm mounted over said blood aspiration tubes on said arraying table, a plurality of air suction needles for sucking air from the inside of said stoppered blood aspiration tubes for evacuation, said air suction needles being carried on a needle rest which is movable mounted on said horizontal arm, driving means for moving said needle rest carrying said air suction needles along a horizontal path and a vertical path over said stoppered blood aspiration tubes arrayed on said arraying table, and for driving said air suction needles with a downward vertical movement into the stoppers of respective ones of said blood aspiration tubes and, after evacuation of said blood aspiration tubes, withdrawing said air suction needles with an upward vertical movement from said stoppers, a presser for pressing said stoppers of said blood aspiration tubes during upward vertical movement of said air suction needles, said presser being mounted to a lower part of said needle rest and being arranged to press said stoppers during upward vertical movement of said air suction needles such that said stoppers are prevented from moving upwards as said air suction needles are withdrawn, an air suction unit for sucking air through said air suction needles so as to evacuate the inside of said blood aspiration tubes with a vacuum, and a controlling device for controlling the operation of said air suction needles, said presser and said air suction unit for automatically sucking air from the inside of said blood aspiration tubes each maintained in a tightly sealed state.

7. The apparatus of claim 6, wherein said presser extends downward from the lower part of said needle rest and has a lower part extending over the stoppers of said plurality of blood aspiration tubes and has a respective plurality of needle apertures formed therein through which said air suction needles are driven downwards and withdrawn upwards.

* * * * *